(12) United States Patent
Folkesson

(10) Patent No.: US 7,908,668 B2
(45) Date of Patent: Mar. 22, 2011

(54) SAFETY EYEWEAR

(75) Inventor: Jan Folkesson, Varnamo (SE)

(73) Assignee: 3M Svenska Aktiebolag, Sollentuna (SE)

( * ) Notice: Subject to any disclaimer, the term of this patent is extended or adjusted under 35 U.S.C. 154(b) by 229 days.

(21) Appl. No.: 11/816,229

(22) PCT Filed: Feb. 3, 2006

(86) PCT No.: PCT/SE2006/000155
§ 371 (c)(1),
(2), (4) Date: Aug. 14, 2007

(87) PCT Pub. No.: WO2006/088408
PCT Pub. Date: Aug. 24, 2006

(65) Prior Publication Data
US 2008/0263754 A1    Oct. 30, 2008

(30) Foreign Application Priority Data
Feb. 15, 2005    (SE) .................................... 0500354

(51) Int. Cl.
*A42B 3/18*    (2006.01)
(52) U.S. Cl. ................................. 2/6.3; 2/448
(58) Field of Classification Search ............. 2/6.3–6.5, 2/6.7, 448–450, 12, 15, 410, 422, 9, 10; 351/155
See application file for complete search history.

(56) References Cited

U.S. PATENT DOCUMENTS

| | | | | |
|---|---|---|---|---|
| 857,838 A * | 6/1907 | Shaw | | 351/155 |
| 860,322 A * | 7/1907 | Paroubek | | 2/10 |
| 1,170,462 A * | 2/1916 | Schroeder | | 2/10 |
| 1,916,678 A | 7/1933 | Malcom | | |
| 2,274,222 A * | 2/1942 | Tedrow | | 2/10 |
| 2,302,231 A * | 11/1942 | Lobelle | | 2/10 |
| 5,289,592 A * | 3/1994 | Paivarinta | | 2/431 |
| 5,752,280 A | 5/1998 | Hill | | |
| 6,424,321 B1 | 7/2002 | Ronzani et al. | | |
| 6,892,393 B1 | 5/2005 | Provost et al. | | |

FOREIGN PATENT DOCUMENTS

EP    0668029    8/1995
EP    0818186    1/1998

OTHER PUBLICATIONS

International Search Report; PCT/SE2006/000155; May 8, 2006.
Supplementary Search Report dated Jul. 13, 2010 for European Application No. 06704544.

* cited by examiner

*Primary Examiner* — Katherine Moran
(74) *Attorney, Agent, or Firm* — Anna A. Wetzels

(57) ABSTRACT

The disclosure relates to safety eyewear disposed in a safety helmet and including a transparent panel for positioning in front of the eyes of the wearer. At each side of the panel, arms are provided which, at their ends are pivotally connected, on the one hand to the panel and, on the other hand, to the helmet. The arms also each have an interjacent joint at a point between their respective ends.

The disclosure also relates to a safety helmet provided with safety eyewear in accordance with the foregoing.

7 Claims, 2 Drawing Sheets

SAFETY EYEWEAR

TECHNICAL FIELD

The present invention relates to eyewear for the wearers of helmets, comprising a transparent panel for positioning in front of the eyes of the wearer, and at least one arm disposed at each side of the panel, the arms being pivotally connected at their ends, on the one hand, to the panel and, on the other hand, to the helmet. The present invention also relates to a safety helmet.

BACKGROUND ART

In different types of work, it is usual to employ safety eyewear, for example to protect the eyes against spatter, dust, radiation etc. A simultaneous use of safety eyewear and hearing protectors—a not uncommon combination—entails a risk that the noise damping inside the hearing protection will be insufficient, since the sidebars or bow of the eyewear extend in between the head of the wearer and the sealing rings of the hearing protection. Another drawback in normal safety eyewear is that they are not often readily available to the user and, as a result, are forgotten. This in turn implies that the risks that would otherwise be avoided by using safety eyewear are still prevalent.

Since the user of the safety eyewear also in quite a number of cases uses a safety helmet in addition to any possible hearing protection, it happens that the safety eyewear is disposed on the safety helmet and is raisable to the space between the helmet and its interior webbing. The webbing of the helmet rests against the head of the user and ensures a good fit on the user's head. Possibly, the webbing is provided with devices for fixing the helmet onto the head of the user.

One prior art solution for safety eyewear entails that the eyewear or glasses, which normally consists of a transparent panel of a plastic material, is provided with grooves at the side edges. Projecting lugs or beads on the helmet webbing are slidable in these grooves so that the safety eyewear is movable in a sliding guide.

A problem with this type of safety eyewear is that it may be difficult to raise or lower, since it shows a tendency to jam if the force for moving the eyewear upwards or downwards is not uniformly applied, in other words in particular if the wearer uses only one hand to raise or lower the eyewear. Another drawback in this construction is that it only displays two entirely stable positions, i.e. the wholly raised position and the wholly lowered position, respectively. The positions between, i.e. along the sliding guide of the panel are not stable. In addition, these positions lie along a completely predetermined path.

In another solution, an arm is provided between the panel and a part of the webbing of the helmet. The arm is pivotal at each end, i.e. on the one hand at the connection to the panel, and, on the other hand, at the connection to the webbing. Possibly, several arms may be disposed adjacent one another, in order to increase stability and the mechanical strength of the construction. This protective panel also moves along a predetermined path, and the possibilities for individual adjustment or adaptation of the safety eyewear are rather limited.

Finally, U.S. Pat. No. 6,511,177 discloses a solution where a set of safety eyewear is secured by an elastic band direct on the hoods of hearing protectors. This solution is best suited for uninterrupted use of the safety eyewear, since there is no natural storage position. The eyewear closely approaches the user's face and the pressure against the face may be perceived by many as uncomfortable in the long term.

There is thus a need in the art to realise a set of raisable safety eyewear which makes possible better adaptation to the individual wearer for increased comfort and, as a result, a greater readiness to use the eyewear.

BRIEF SUMMARY OF INVENTION

The invention provides eyewear including arms which each display an interjacent joint at a point between their respective ends.

BRIEF DESCRIPTION OF THE ACCOMPANYING DRAWINGS

The present invention will now be described in greater detail hereinbelow, with reference to the accompanying Drawings. In the accompanying Drawings.

DESCRIPTION OF PREFERRED EMBODIMENT

Figure 1:
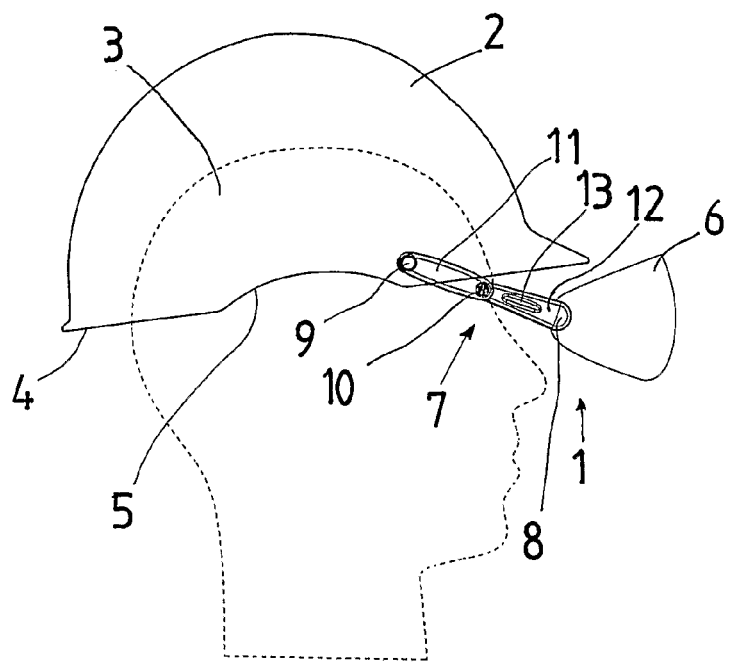
FIG. 1 is a schematic view of safety eyewear according to the present invention in a position of maximum protraction.

FIG. 1 shows a set of safety eyewear 1 according to the present invention mounted on a helmet 2. The head 3 of the wearer of the helmet is intimated by broken lines.

The helmet 2 is provided with webbing 16 (shown in FIG. 2) which rests on the wearer's head and which may be adapted to the shape and size of the wearer's head. As a result of the interior webbing 16, the head is not in direct contact with the inside of the helmet 2 and impact and jolts to which the helmet is subjected from outside are not directly transmitted to the head 3 but are absorbed, at least partly, by the interior webbing 16. The webbing 16 is typically the place where the safety eyewear 1 according to the invention are secured even if it is per se conceivable to employ a solution where the fixing points of the safety eyewear 1 are disposed directly in the helmet 2.

Between the helmet interior webbing 16 (shown in FIG. 2) and the helmet 2 proper, i.e. its outer shell, there is a space in which the eyewear 1 may be movable into a storage position. At the lower edge 4 of the helmet 2, there are provided recesses that make it possible for hearing protection to be worn simultaneously with the helmet. However, the presence of these recesses 5 is optional depending on the rest of the design of the helmet. The essential feature for the present invention is that the safety eyewear 1 neither presupposes the wearing of hearing protection, is prevented thereby, nor prevents effective noise damping in the hearing protection.

The eyewear 1 comprises a panel 6 which is intended to be positioned in front of the eyes of the wearer. The panel 6 may liken conventional eyeglasses, possibly be provided with a recess for the nose of the wearer, or otherwise extend a distance down in front of the face of the wearer in a manner similar to a visor. The panel 6 is manufactured from a totally clear material or toned material depending on the contemplated field of use. Possibly, the panel 6 may be manufactured from such material as is suitable as eye protection in welding operations.

On each side of the panel 6, there is disposed an arm 7 whose outer end 8 is secured at the panel 6 and whose inner end 9 is secured in the helmet 2 or its interior webbing 16. The arm 7 is pivotal at both its outer end 8 and its inner end 9. As a result, the panel 6 may be angled in relation to a vertical line, since it is pivotal about an axis that extends through both of the outer ends 8 of the arms 7 at each respective side of the panel 6. Since the panel 6, together with the arms 7, is also pivotal around the inner ends 9 of the arms 7, this implies that the panel 6 moves along an arcuate path in front of the face of the user, i.e. a movement in the height direction will be obtained. The mobility in the joints at the ends 8 and 9 is such that a desired position may quite simply be set, but that the set position is maintained until another position is chosen.

Centrally on each respective arm 7, there is disposed an interjacent joint 10. Thus, the arm 7 is divided into an inner link 11 and an outer link 12. In FIG. 1, the arm 7 is shown in its position of maximum protraction, but it a bending takes place of the interjacent joint 10, the inner link 11 will be angled in relation to the outer link 12 instead of lying in line with it. This implies that the effective distance between the outer end 8 of the arm and its inner end 9 is reduced. On a shortening of the arm 7 in this manner, the safety eyewear 1 will be pivotal about the inner end 9 along another arcuate path than that which applies when the arm 7 is in its position of maximum protraction. This adjustment is stepless and implies, together with the possibility of angling the panel 6 around the outer ends 8 of the arms 7, that the safety eyewear may be adjusted to a very large number of positions in the area in front of the face of the user, which further implies excellent adjustment possibilities and adaptation to suit different individual wearers. The interjacent joint 10 is also sufficiently stiff to remain in its adjusted position, but sufficiently movable to permit a new adjustment.

For simple use of the safety eyewear, each respective outer link 12 is provided with a hand grip 13. The hand grip 13 may assume the form of a groove or slot or other depression, but may also consist of a roughened surface which affords better grip for the fingers on adjustment of the eyewear 1. The hand grip may also be a strip or a protruding embossment or bead. In order for it still to be possible to angle the links 11 and 12 in relation to one another, it may be necessary for them to change places compared with that illustrated in the Figures, so that the projection faces away from the inner link 11.

Figure 2:
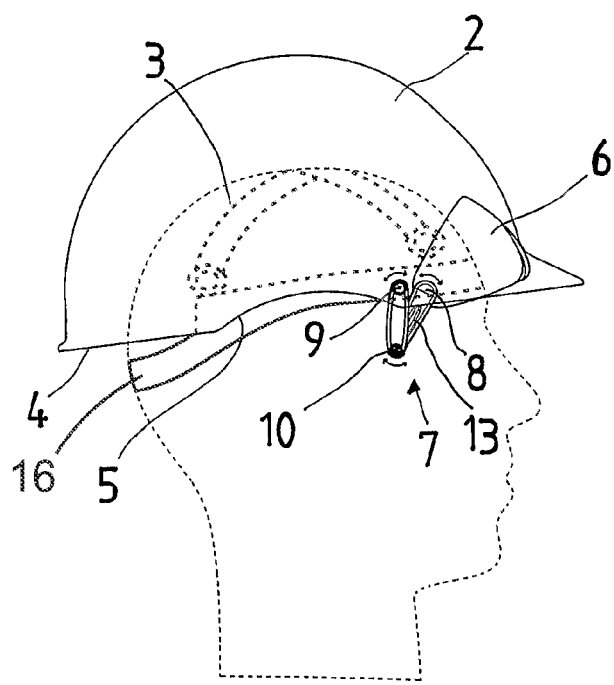
FIG. 2 is a schematic view corresponding to that of FIG. 1 of the eyewear in a storage position.

FIG. 2 shows the eyewear 1 in the raised position of storage. In this instance, the arm 7 has been greatly folded together and its outer end 8 is located at a very short distance from the inner end 9. The effective length of the arm 7 is thus extremely short, practically the shortest length that can be achieved. In the storage position, the panel 6 is also angled so that it assumes a position which makes possible insertion in between the outer shell of the helmet 2 and its inner webbing 16. The angle of the panel 6 in relation to a vertical line thus differs from its angle in relation to the vertical line according to FIG. 1. In FIG. 2, the pivotal action in the points 8, 9 and 10 has also been marked.

Figure 3:
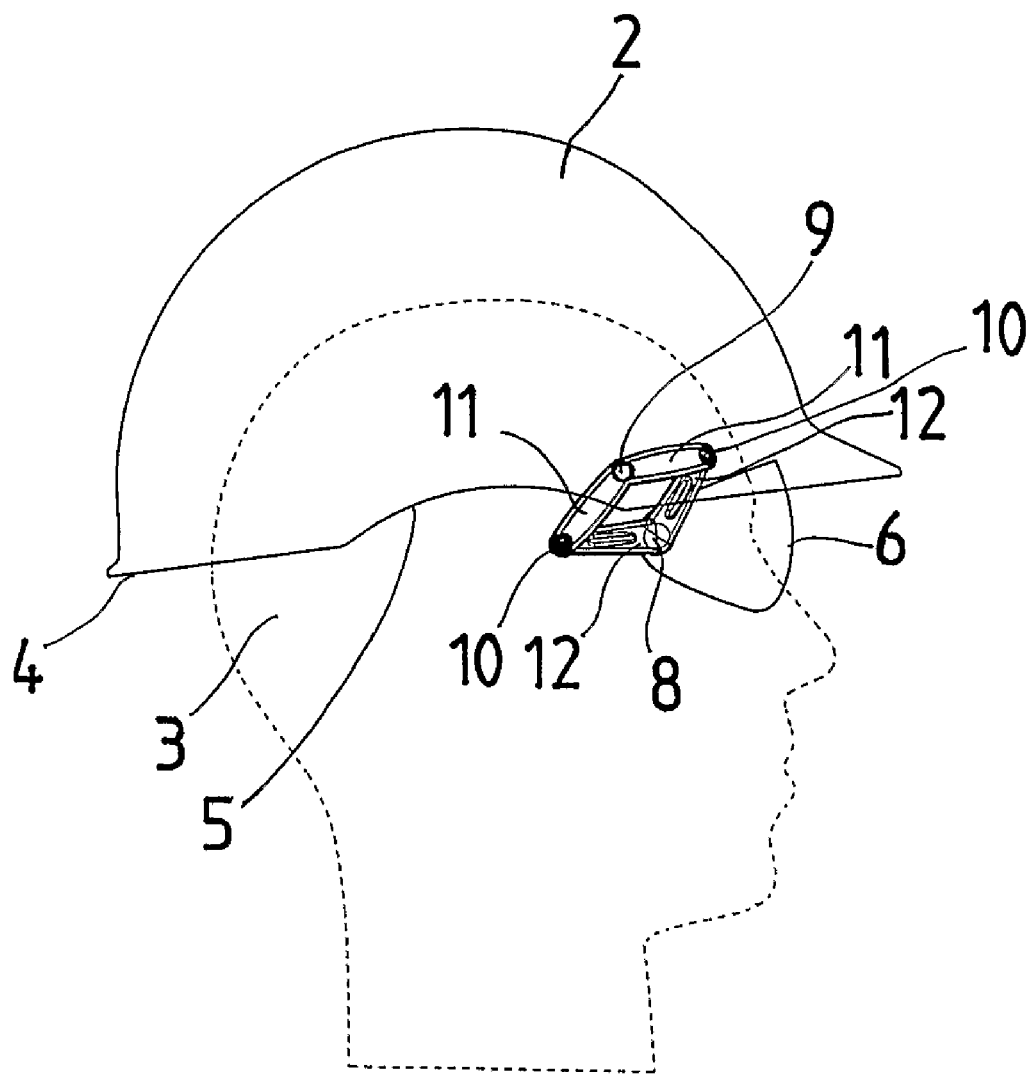
FIG. 3 is a schematic view corresponding to that of FIGS. 1 and 2 of a position of use where two alternative positions of the arms are illustrated.

FIG. 3 shows the safety eyewear 1 in a position of use. It should be emphasised that the arm 7 is shown in two different positions which are both possible when the panel 6 assumes the illustrated position. In the one position, the greater part of the arm 7 is located outside the helmet 2, more precisely the outer link 12 and approximately half of the inner link 11. In the alternative position of the arm 7, the inner link 11 is located inside the helmet, while roughly half of the outer link 12 is visible outside the helmet. That which is common to the two alternative positions of the links included in the arm 7 is that the distance between the outer end 8 of the arm 7 and its inner end 9, i.e. the effective length of the arm, is the same. It is thus the effective length of the arm 7 together with the angling of the panel 6 around the fixing points in its outer ends 8 that is decisive for the exact position of use, and that permits an extremely accurate individual adaptation. It could be said that the size of the effective length, as well as the angle to a vertical line differ in FIGS. 1, 2 and 3 where the safety eyewear, in turn assume a maximum protracted position, a storage position and finally a position of use.

In order that the safety eyewear function to the maximum, the point 8, 9 and 10 should be movable also in those cases when their axes are not parallel with each other. In such instance, possible manufacturing intolerances will have no effect on function and a certain angle between the two anus 7 may be permitted when the safety eyewear is manufactured.

If the distance between the two inner ends 9 of the arms 7 differs from the distance between the two outer ends 8, it might moreover be necessary for the arms to be flexible or curved, or possibly both. However, the important feature is that their effective length is variable. The present invention may be further modified without departing from the scope of the appended Claims.

What is claimed is:

1. Safety helmet, comprising an eyewear having a transparent panel for positioning in front of eyes of the wearer and at least one arm disposed at each side of the panel, each arm being pivotally connected at one end to the panel and at another end to the helmet, wherein the arms also each have an interjacent joint at a point between their respective ends, and wherein the panel is movable between a position of use and a storage position inside the helmet;

wherein the helmet has an outer shell and an interior webbing and wherein the panel in the storage position is disposed between the interior webbing and the outer shell of the helmet.

2. The safety helmet as claimed in claim 1, wherein each respective arm may be angled in the interjacent joint for a variation of the distance between an outer and an inner fixing points of the arms.

3. The safety helmet as claimed in claim 1, wherein a length of the arms is such that a point in the position of maximum protraction of the arms is located a distance in front of a normal position of use.

4. The safety helmet as claimed in claim 1, wherein axes of the joints are substantially horizontal.

5. The safety helmet as claimed in claim 1, wherein the transparent panel includes a recess for a nose of a wearer.

6. Safety helmet, comprising an eyewear having a transparent panel for positioning in front of eyes of the wearer and at least one arm disposed at each side of the panel, each arm being pivotally connected at one end to the panel and at another end to the helmet, wherein the arms also each have an interjacent joint at a point between their respective ends, and wherein the panel is movable between a position of use and a storage position inside the helmet, wherein each arm comprises an inner link and an outer link connected by the interjacent joint, each outer link having a hand grip.

7. Safety helmet, comprising an eyewear having a transparent panel for positioning in front of eyes of the wearer and at least one arm disposed at each side of the panel, each arm being pivotally connected at one end to the panel and at another end to the helmet, wherein the arms also each have an interjacent joint at a point between their respective ends, and wherein the panel is movable between a position of use and a storage position inside the helmet, wherein the helmet comprises an interior webbing and inner fixing points of the arms are disposed in an interior webbing of the helmet.

* * * * *